United States Patent [19]

Ritter

[11] Patent Number: 5,478,343
[45] Date of Patent: Dec. 26, 1995

[54] TARGETING DEVICE FOR BONE NAILS

[75] Inventor: Gebhard Ritter, Mainz, Germany

[73] Assignee: Howmedica International, Inc., Shannon, Israel

[21] Appl. No.: 278,712

[22] Filed: Jul. 22, 1994

Related U.S. Application Data

[63] Continuation of Ser. No. 893,622, Jun. 5, 1992, abandoned.

[30] Foreign Application Priority Data

Jun. 13, 1991 [DE] Germany ............................ 9107298 U

[51] Int. Cl.⁶ ........................................................ A61F 5/04
[52] U.S. Cl. .................................... 606/97; 606/98; 606/96
[58] Field of Search ........................ 606/96–99, 102–104, 606/80, 86, 87, 64, 67; 378/204; 128/653.1

[56] References Cited

U.S. PATENT DOCUMENTS

| | | |
|---|---|---|
| 4,722,336 | 2/1988 | Kim et al. . |
| 4,803,976 | 2/1989 | Frigg .......................................... 606/97 |
| 4,848,327 | 7/1989 | Perdue . |
| 5,013,317 | 5/1991 | Cole ........................................... 606/96 |
| 5,030,222 | 7/1991 | Calandruccio ............................. 606/80 |
| 5,147,367 | 8/1992 | Ellis ........................................... 606/60 |

FOREIGN PATENT DOCUMENTS

| | | |
|---|---|---|
| 405132 | 2/1991 | European Pat. Off. ................. 606/80 |
| 495488 | 6/1992 | European Pat. Off. ................. 606/96 |
| 518071 | 12/1992 | European Pat. Off. ................. 606/96 |
| 223918 | 6/1985 | Germany . |
| 0167719 | 1/1986 | Germany . |
| 0201737 | 11/1986 | Germany . |
| 250255 | 8/1987 | Germany . |
| 0281763 | 9/1988 | Germany . |
| 0358579 | 3/1990 | Germany . |
| 3205404 | 9/1983 | Switzerland ............................. 606/98 |
| 668692 | 1/1989 | Switzerland . |
| 671873 | 10/1989 | Switzerland . |
| 1489733 | 6/1989 | U.S.S.R. ................................... 606/96 |

OTHER PUBLICATIONS

*Journal of Bone and Joint Surgery*, British Ed. "Boppe's Goniograph".
Grosse & Kempf catalog Nov. 1988.
Plus European Search Report E. O. Slade Jan. 18, 1994.
P. 59 "Victor Extension Cylinder" from ]*X–Ray Supplies* by General Electric.
*Journal of Bone & Joint Surgery*, British Ed. "Boppe's Goniograph".

*Primary Examiner*—Robert A. Hafer
*Assistant Examiner*—David J. Kenealy
*Attorney, Agent, or Firm*—Peter C. Richardson; Lawrence C. Akers; Elizabeth O. Slade

[57] ABSTRACT

A targeting device for making holes in cortical bone for bone nails has a right angle drill which interconnects to a telescopic guide member. The guide member attaches to the drill at the side thereof opposite the chuck. The free end of the telescopic guide attaches to an X-ray machine and maintains the drill in position during the drilling operation. A manual targeting device is used to locate bores in the bone nail and to spot drill the bone. The aligned telescopic guide is then used to complete the drilling operation.

18 Claims, 6 Drawing Sheets

TARGETING DEVICE FOR BONE NAILS

This is a continuation of application Ser. No. 07/893,622, filed on Jun. 5, 1992 now abandoned.

BACKGROUND OF THE INVENTION

1. Field of the Invention

The invention relates to a device for making holes for the implantation of interlocking bone nails.

2. Description of the Prior Art

Interlocking nails are used for bone fractures and have transverse bores for fixation within the bone by bone screws. Such a nail is shown in U.S. Pat. No. 4,976,258. The screws secure the nail against relative axial and rotational movement. The interlocking nails are inserted proximally, for example in the femur, and the distal portion of the nail normally has two transverse bores so that aligned bores or holes must be made in the conical bone. The correct positioning of the transverse bores within the bone is relatively difficult and requires additional instrumentation. For this purpose, targeting devices are used in combination with an X-ray source and an X-ray image converter.

Manually operable unsupported targeting devices are known as well as devices attached to a relatively stationary targeting system. The direct attachment of the targeting device to an image converter enables an accurate placement of the holes. A displacement of the leg of a patient or of the surgical table causes a misalignment.

The German Gebrauchsmuster 84 17 428 (U.S. Pat. Nos. 4,625,718 and 4,850,344) discloses an apparatus which combines a targeting device with a power-driven drilling tool in that a radiation transparent chuck is used. The drill bit is projected as a spot if it is extended parallel to the radiation direction.

The EP-A-O 201 737 discloses a targeting device including a drill sleeve connected to a handle and a sighting device connected to the sleeve, with the position of the sighting device between a radiation source and a radiation receiver made visible through an image converter. A sighting device separate from the drilling sleeve has the advantage that the control and correction of the targeting device can be carried out during the drilling process. However, it is disadvantageous that a target element must be attached to the drilling sleeve prior to the detection of the drilling axis by means of the sighting device. A target element may consist of a radiation transparent pin having a radiation-impervious spot at the tip. By using the sighting means and the target pin, the drill sleeve can be accurately positioned against the bone. After repeated alignments with the sighting device, the hole is made by guiding the drill bit in the drilling sleeve.

The German Gebrauchsmuster 87 03 438 discloses an auxiliary instrument for the setting of holes wherein a guiding member is attached to a handle and is made of a material transparent for X-rays. The guiding member includes a guiding bore for the slidable guidance of a rod-shaped punching tool. The guiding member includes two axially spaced annular members encircling the guiding bore which appear in an overlapped formation on the screen if the X-rays are aligned with the guiding bore.

The described manually operable devices require a permanent correction of the position of the drilling sleeve during the drilling process in order to insure that both the first and second bores in the cortical bone are accurately positioned. This correction is made by the X-ray device. Examples of related targeting devices are described in U.S. Pat. Nos. 4,917,111, 5,013,317 and 5,030,222.

SUMMARY OF THE INVENTION

It is an object of the invention to provide a device for setting holes for the implantation of interlocking nails that is simple to use, allows an exact placement of the holes and reduces the exposure rate of the surgeon to X-rays.

The device according to the present invention includes a drill with a right angle drive having a coupling fitting attached to the surface thereof opposite to the chuck which holds the drill. The coupling fitting is adapted to accommodate a telescopic guide member. The free end of the guide member (opposite the end attached to the coupling) is adapted to engage the window of the image converter or the front portion of the housing of the X-ray source such that the axis of the guide member is coaxial with the X-ray beam axis.

The device according to the present invention makes use of the fact that it is relatively simple to detect the point on the conical bone through which the axis of both coaxial bores extends. This point on the bone can be marked in a suitable manner, e.g. by means of a bone pin or a drill bit. For example, the cortical bone can be spot drilled at this point to ensure that the drill bit does not slide away when the first and the second conical bone are drilled. It is decisive that the drill bit be guided along the axis through the locking bores in that the drilling tool with the drill bit is aligned accordingly, with the drill bit engaging the mentioned spot.

This is achieved with the aid of the telescopic guiding member which can be relatively rigidly connected to the right angle drill while its other end engages the window of the image converter or the front housing portion of the X-ray source. For the sake of explanation, it is to be noted that the X-ray source may be placed above the operation area and directly radiate this area or it may be placed on the opposite side, depending on the method used. The image converter is then placed on the side opposite the source. If the X-ray source is located above the operation area, the guide member is brought into engagement with the housing of the X-ray source. Conventional X-ray sources have a conical front portion. Accordingly, the guide member has an inner cone to be plugged on the outer cone of the housing on the front of the X-ray source. Since the axis interconnecting the X-ray source and the image converter is aligned with the axis of the coaxial locking bores (this is mandatory for the precise setting of the holes for the implantation of interlocking nails). The drill is aligned correspondingly and is continuously guided during the drilling process since the telescopic guide member is extended longitudinally during the drilling process and thus maintains its guiding function.

If, however, the image converter faces the operation area, an engagement surface at the free end of the guide member engages the window of the image converter. To this purpose, the telescopic guide member is extended up to the window of the image converter, and the assistant who is looking for the desired orientation of the guide member makes sure that the flat engagement surface on the guide member is placed flush with the window. When this is done, the drilling tool is precisely aligned and the drilling process can be started. Appropriately, the guide member is continuously held in engagement with the window of the image converter during the drilling process.

From the above explanation of the function of the device according to the present invention, it can be seen that the X-ray source should not be turned on during the alignment process of the guide member and the drilling process. Thus, the surgeon is not subject to any radiation during these process steps.

From the above-described targeting device it is known to provide a sleeve-like target member which also serves for the guidance of the drill bit. However, in order to find out the engagement point on the first cortical bone for the drill bit, the target sleeve must be exactly aligned with the X-ray beam with respect to all planes. If the sleeve is not accurately aligned, it is impossible to align the bore of the sleeve with respect to the holes in the interlocking nail accurately. When this engagement point has been found, the next problem is to not displace the sleeve during the drilling process and to maintain its position during the insertion of the drill bit and during the drilling process because no realignment can be carried out during the drilling process. Therefore, one embodiment of the invention includes a hollow funnel-like target member having an upper portion which tapers conically upwardly while the lower opening corresponds to the outer diameter of the drill bit.

Therefore, the present invention does not use a cylindrical drilling sleeve as the targeting member, but rather, a kind of funnel. With such a hollow conical drilling sleeve only the exit of the funnel has to be aligned with the bores of the nail on the monitor of the X-ray image converter while the other position or attitude of the funnel can be disregarded.

The surgical operation is relatively simple. After the soft tissue incision has been made, the funnel is first brought into engagement with the bone. Thereafter, the image converter is switched on. The exit opening of the funnel can be simply aligned with the locking bores. In case the opening of the funnel on the X-ray monitor is circular, then the lower opening of the funnel is exactly aligned with the locking bores of the nail. Thus, the engagement point for the drill bit has been detected. This targeting process requires only a few seconds and is the single phase wherein an X-ray illumination is necessary for the setting of the holes. The further steps do not require the use of any X-rays. Thus, the surgeons are not subject to an additional X-ray load. After the positioning of the funnel, the drill bit is introduced by means of the right angle drill. The exact angular position of the drill can be disregarded. The bone is merely spot-drilled in order to achieve an engagement point for the major drilling process. This short spot-drilling can be made during a period of 2 to 3 seconds.

According to another embodiment of the invention, the target member is cylindrical above the conical funnel portion, and a second sleeve for use as a guide sleeve is located between the handle and the target member. The axis of the second sleeve has a distance from the axis of the target member which corresponds to the distance between the pairs of locking bores, In the preferred embodiment, a guide bushing is introduced into the second sleeve, the cortical bone can be spot-drilled with respect to the second pair of locking bores.

These and other objects and features of the present invention will become apparent from the following detailed description considered in connection with the accompanying drawings, which disclose several embodiments of the invention. It is to be understood that the drawings are to be used for purposes of illustration only, and not as a definition of the limits of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
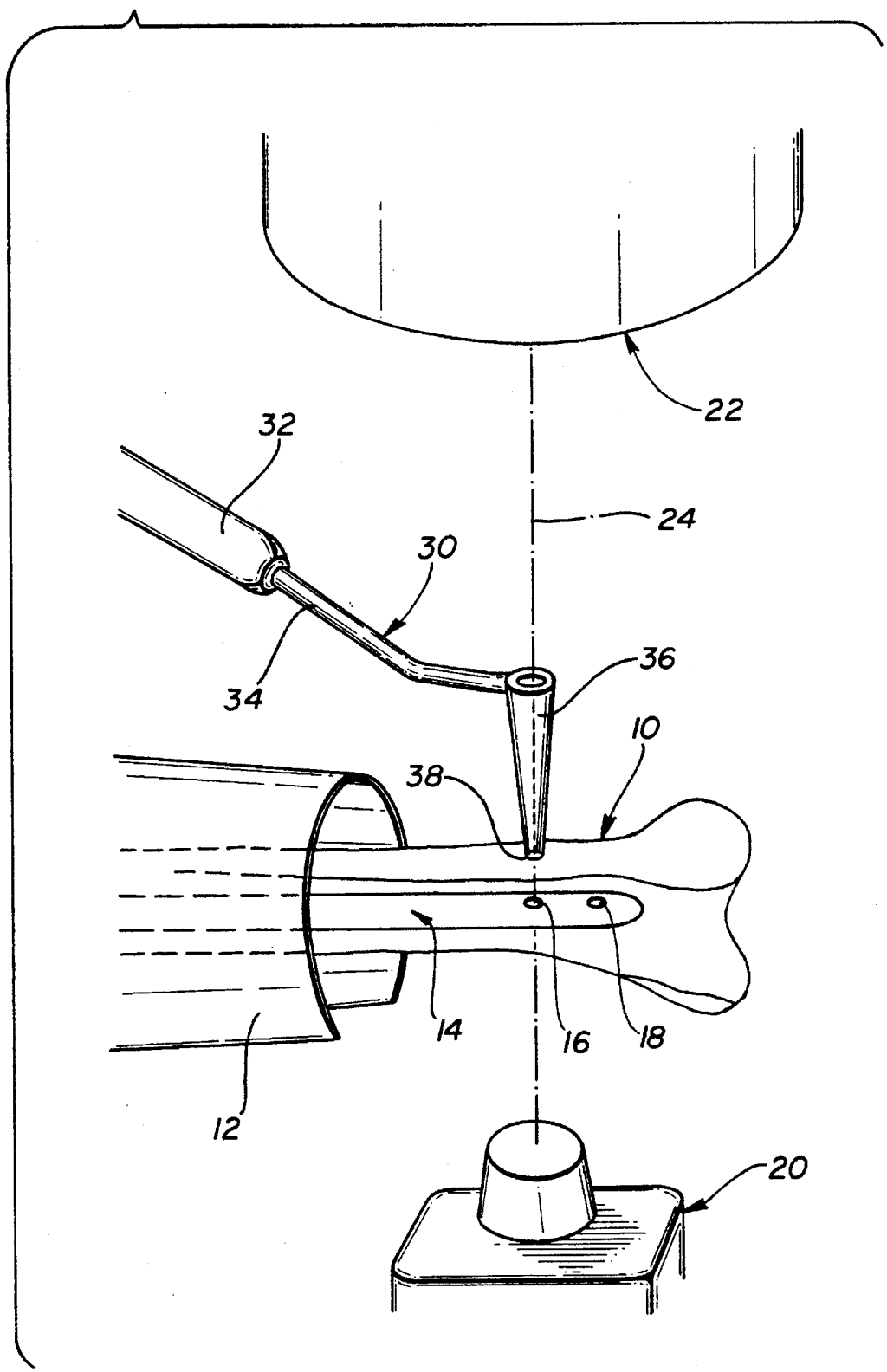
FIG. 1 is a diagrammatic perspective view of the targeting device according to the present invention.

Referring to FIG. 1, there is shown a distal femur portion 10 of a patient who has been placed on an operating table (not shown). The proximal area of the leg is covered by a sheet 12 of lead. Conventional interlocking nail 14 is introduced into femur 10 proximally. Nail 14 has two pairs of distal locking holes 16, 18.

An X-ray device includes an X-ray source 20 below femur 10 and an image converter 22 above the femur. The axes of image converter 22 and of X-ray source 20 are aligned as indicated by dashed line 24. X-ray source 20 and image converter 22 are rigidly interconnected as is the case with most standard X-ray machines. Such a rigid interconnection being a standard structural feature on all commercial X-ray machines, such is not shown. For setting the holes in the cortical bone of the femur 10, the X-ray source and converter are aligned such that the axis 24 extends through both holes of each pair of holes 16 or 18, respectively. This happens when both locking holes of a pair overlap each other and appear on the window of the image converter 22 or the respective monitor, respectively, as a single circle.

The targeting device 30 of the present invention has a handle 32, a shank 34 and a hollow funnel-shaped conical target sleeve 36 at the end of the shank. The edge of the lower opening of sleeve 36 has teeth 38 best seen in FIG. 7. The diameter of the lower opening of the sleeve 36 is slightly larger than the outer diameter of the drill bit used to bore the cortical bone.

Figure 2:
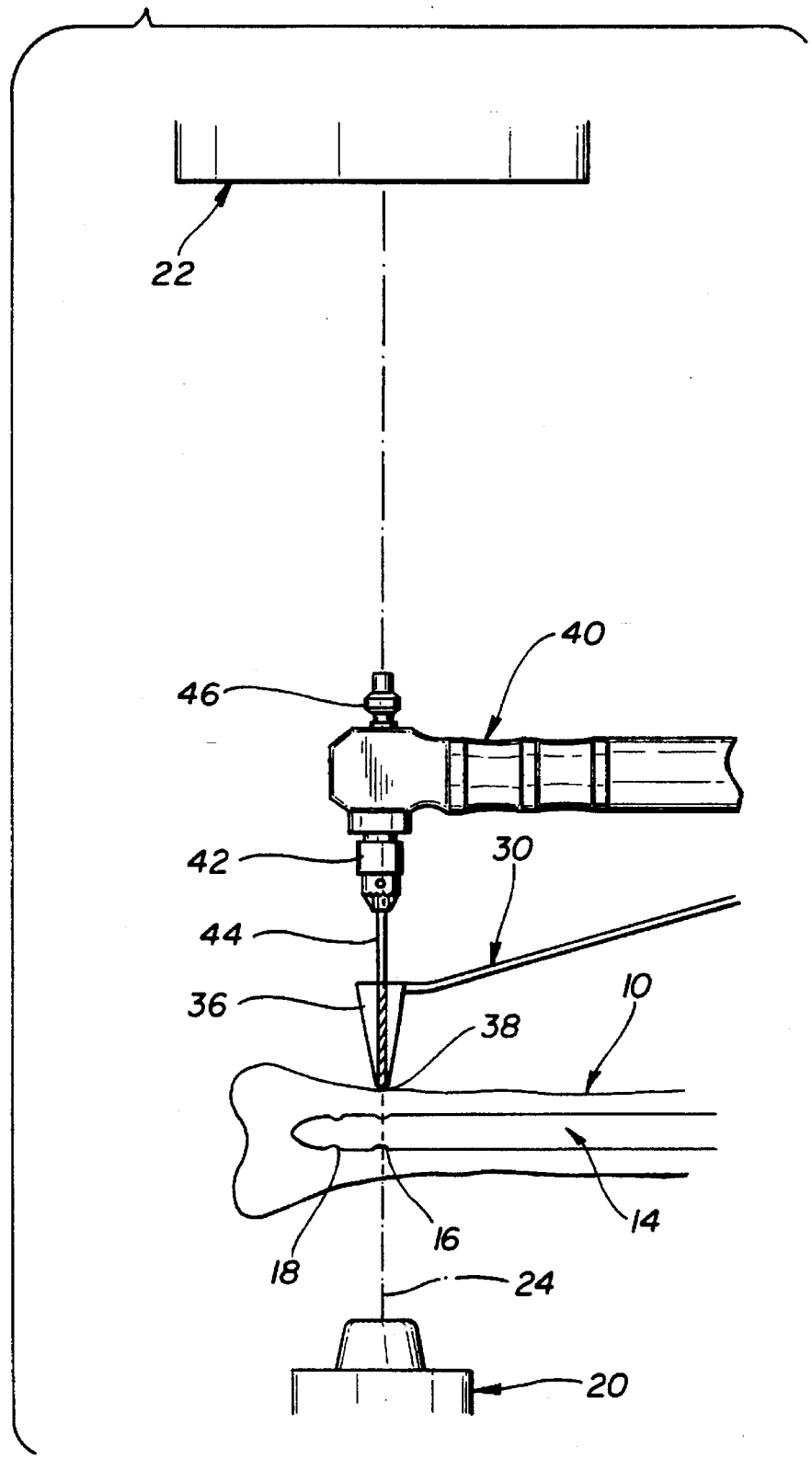
FIG. 2 is a side view of the device of FIG. 1 during a first operational phase.
Figure 3:
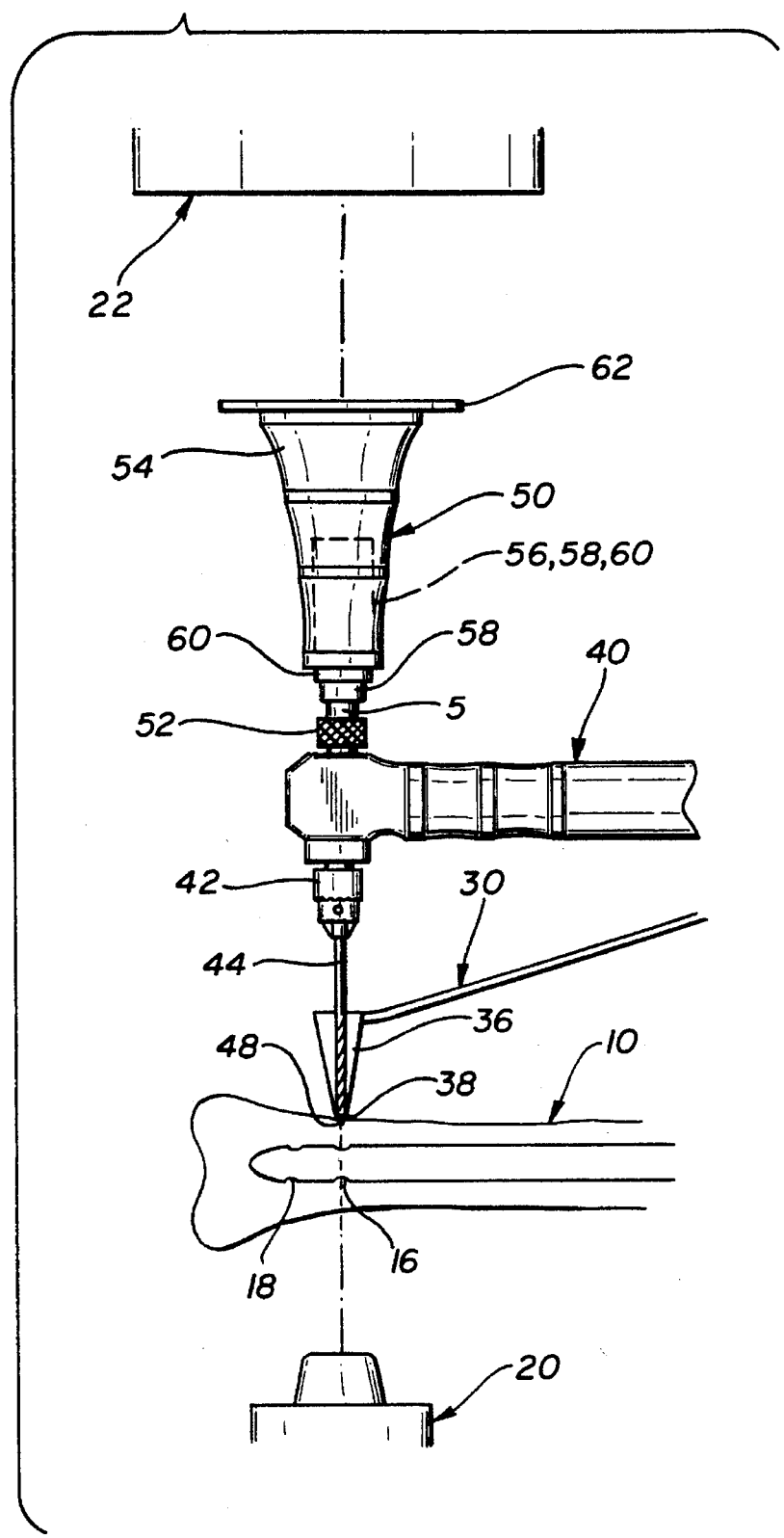
FIG. 3 is a view similar to FIG. 2 in a successive operational phase.

After the incision of the soft tissue is made, target sleeve 36 is brought into engagement with the bone. Thereafter, X-ray source 20 and image converter 22 are turned on. By observation of the monitor (not shown), lower edge 38 of sleeve 36 can be brought into alignment with the locking holes. The opening of sleeve 36 is circular and open and can easily be exactly aligned with a respective pair of holes 16 or 18 of nail 14. This targeting procedure requires only 3 to 10 seconds at the maximum X-ray illumination. Thereafter, the cortical bone is spot-drilled. This can be seen in FIGS. 2 and 3. A right angle drive drill 40 is located below image converter 22. A drill bit 44 is clamped in a chuck 42 mounted on drive 40. On the end of drill 40 opposite to the chuck 42, a quick-coupling fitting 46 is located. The drill bit 44 is inserted into the target sleeve 36 in order to spot-drill the femur 10 as indicated in FIG. 3 at 48. During this process, the exact position of the corner drill can be disregarded because the angle of drill bit 44 is unimportant.

Figure 4:
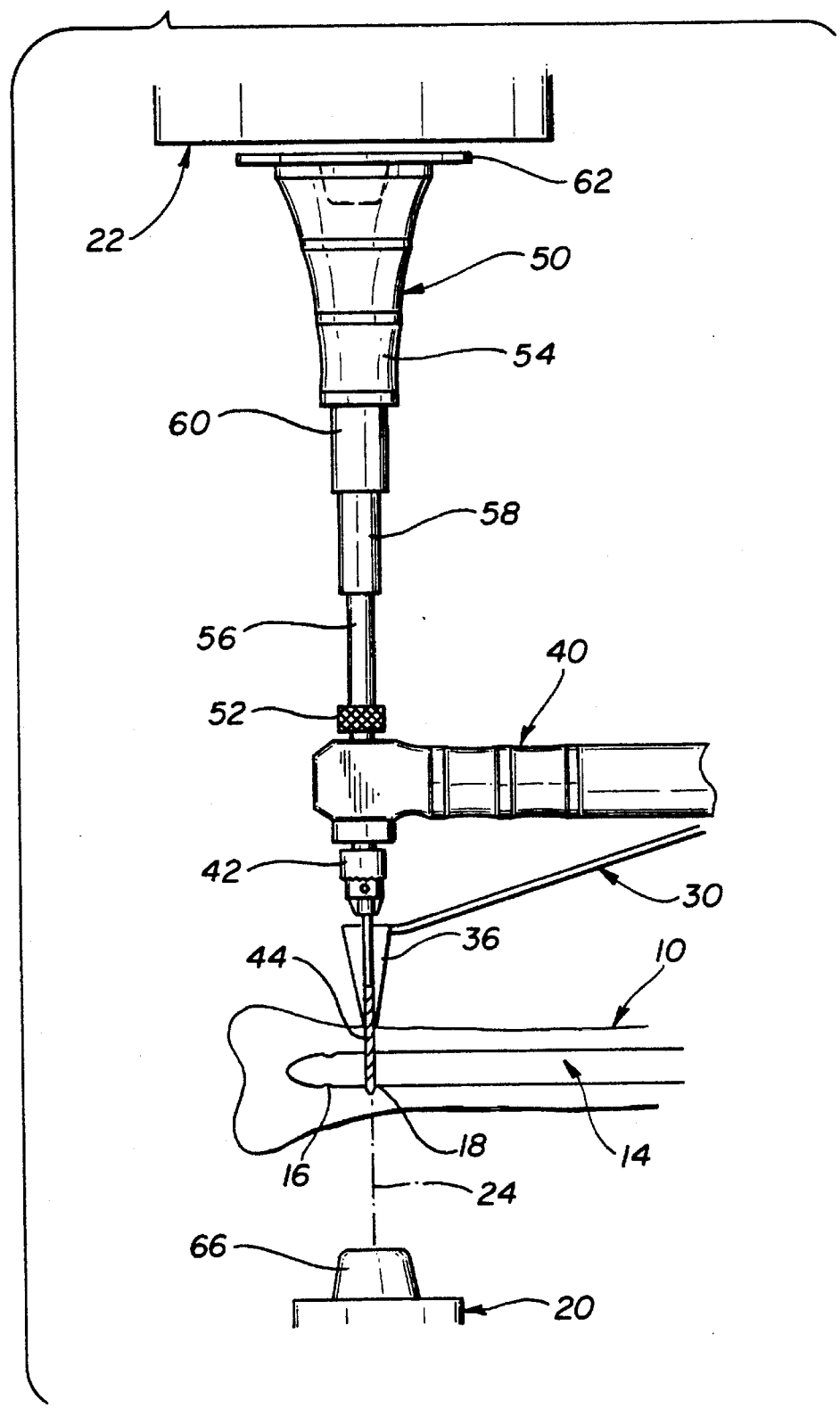
FIG. 4 is a view of the device of FIG. 2 during the drilling phase.
Figure 5:
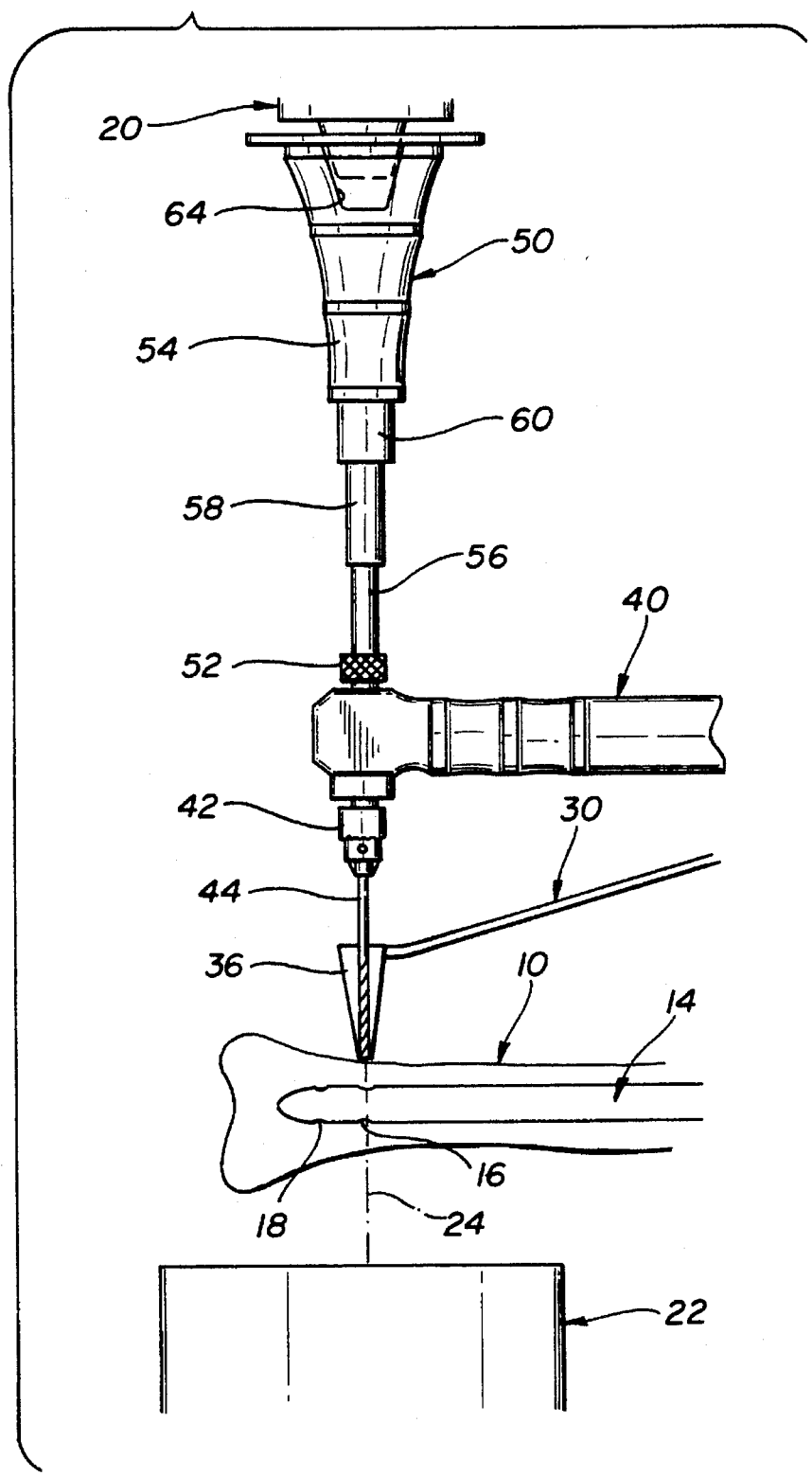
FIG. 5 is a view similar to FIG. 2 with the X-ray machine in a second position.

A telescopic guiding member 50 is then coupled to drill 40. This is accomplished by means of a coupling portion 52 on guiding member 50 coupling with the coupling portion 46. As can be seen in FIGS. 4 and 5, guide member 50 includes a conical receiving or retaining portion 54 and in addition has three cylindrical tubular portions 56, 58 and 60 which are telescopically interconnected and can be pushed together and received in conical portion 54 (as can be seen in FIG. 3). At the free end of the conical portion 54, an annular disc 62 is provided defining a flat engagement surface. Within the area of the engagement disc 62, an inner conical bore 64 is provided in the conical telescoping portion 54 as can be seen in FIG. 5.

When guide member 50 is attached to drill 40 as shown in FIG. 3, guide member 50 is telescopically extended as shown in FIG. 4. The engagement disc 62 is brought into engagement with the entrance window of the image converter 22 such that it lies completely against the window over its circumference. The outer circumference of disc 62 may be shaped and sized to match the entrance window shape.

Consequently, drill 40 is located in a position wherein the axis of drill bit 44 is coaxial with axis 24. When drill bit 44 pierces through the first cortical bone as shown in FIG. 4, it can be extended through both locking holes 18 and can drill the second cortical bone bore subsequently. During this process, guide member 50 is telescopically extended without losing its guiding function. For this, it is mandatory that the engagement disc 62 be continuously held flush against the window of image converter 22.

In some systems, the location of the X-ray source and the image converter 22 is reversed. This is shown in FIG. 5. It can be seen that the housing of the X-ray source has a conical portion 66 at the front end. The cone 64 of portion 54 of guide member 50 fits onto the conical housing portion 66 so that an alignment of guide member 50 with respect to axis 24 of the X-ray device can also be achieved.

Figure 6:
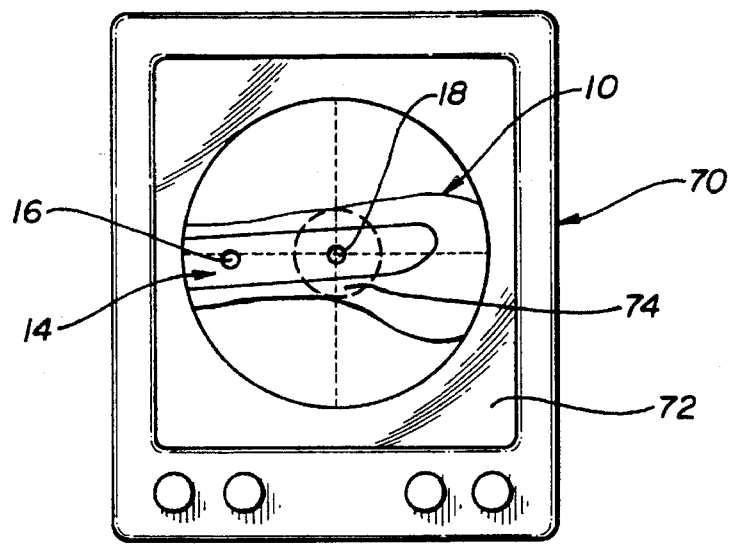
FIG. 6 is a diagrammatic view of the monitor showing the alignment of the target member with respect to an interlocking nail.

In FIG. 6 an image of the femur and of the interlocking nail on a screen 72 of a monitor 70 is shown. A sheet 74 having a circle thereon with, for example, a diameter of 50 mm, is adhered to the screen in the center thereof. If both pairs of holes 16, 18 of nail 14 respectively are placed on a diameter within the circle, the image converter device is sufficiently aligned with respect to the bores in interlocking nail 14. Then, the process described above can be carried out for both pairs of locking holes 16, 18.

Figure 7:
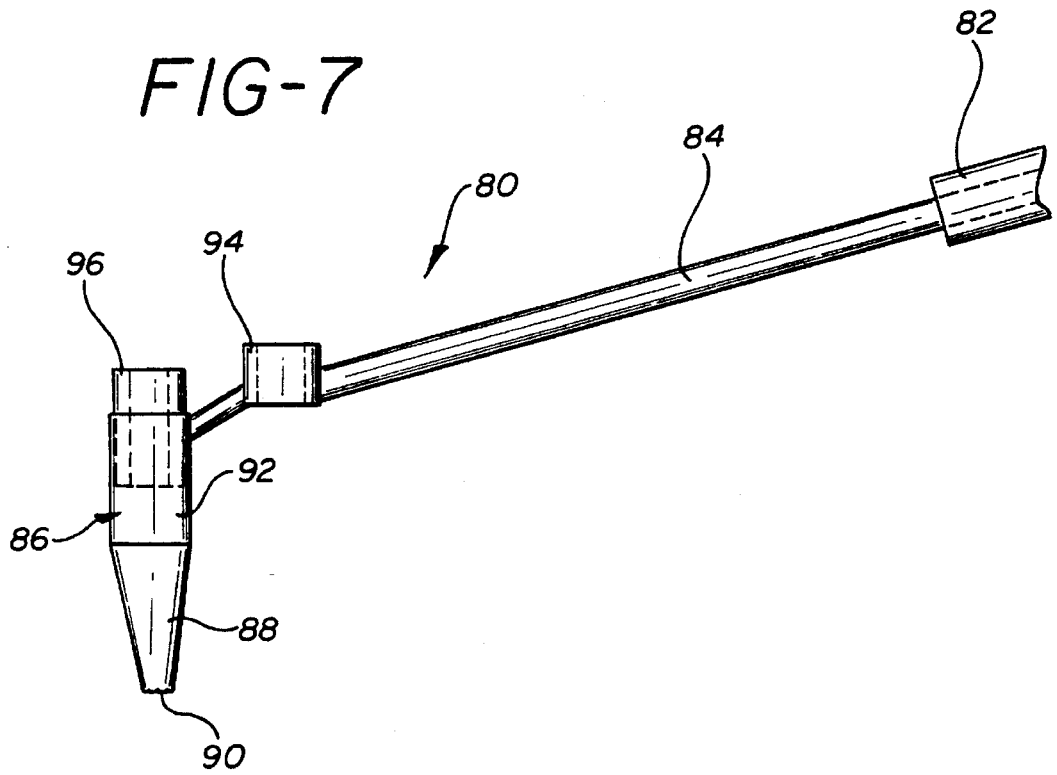
FIG. 7 is a side view of an alternate embodiment of the targeting device.

In an additional embodiment of the invention as shown in FIG. 7, a manually operable target device 80 is provided. Device 80 is used to preform the spot drilling of the femur at the two spaced locations corresponding to holes 16, 18. Device 80 has a handle 82, a shank 84 and a target sleeve 86. The target sleeve has a conical portion 88, with a lower opening having a toothed edge 90. A cylindrical portion 92 is located above the conical portion 88.

A second guide sleeve 94 spaced from the target sleeve 86 is located on shank 84. The axis of the target sleeve 86 and the guide sleeve 94 are spaced from each other with the distance corresponding to the distance between the locking bores 16, 18. The first spot drill can be made with the target device 80 of FIG. 7 in the same manner as described in connection with FIGS. 1 to 5. In addition, drilling through the cortical bone by means of the target sleeve is accomplished in the manner explained above. The drill bit 44 extending through the cortical bone and the holes 16 of interlocking nail 14 can be removed from the chuck of drill 40 while still extending through target sleeve 86.

An auxiliary sleeve 96 corresponds to the inner diameter of cylindrical portion 92 while the inner diameter corresponds to the outer diameter of drill bit 44. When the auxiliary sleeve 96 is inserted into the target sleeve 86, the target sleeve 86 is coaxial to the axis of the locking holes 16. This places guide sleeve 94 at a distance from the axis through holes 16 which corresponds to the distance between the pairs of locking holes 16 and 18. An alignment of the guide sleeve in a plane perpendicular to this axis takes place by the X-ray device. For this purpose, the X-ray source is switched on again so that an aligning process can take place within a short time in order to drill the cortical bone in alignment with the second pair of locking holes 18.

It can be seen that a pin can be inserted through the first pair of holes 16 in the cortical bone instead of a drill bit in order to achieve the axial alignment of the guide sleeve 94 by means of the auxiliary sleeve 96.

While several embodiments of the present invention have been described, it is obvious that many changes and modifications may be made thereunto, without departing from the spirit and scope of the invention.

I claim:

1. A device for making holes for precisely implanting into a cortical bone a locking nail having an axis and having at least one distal locking bore, said device to be used with an X-ray source having a housing and a beam axis and with an associated image converter having an entrance window and an axis perpendicular to said window and to be used such that said beam axis is simultaneously coaxially aligned with said axis perpendicular to said window and with said distal locking bore when said bone is being drilled, said device comprising in combination:

a drilling tool for drilling a first hole in said cortical bone coaxially with the axis of said distal locking bore, wherein said drilling tool comprises a right angle drive drill having a chuck and a coupling fitting located opposite to said chuck; and a guide means for guiding said drilling tool, wherein said guide means includes a means for telescoping in a direction perpendicular to said axis of said locking nail and parallel to said X-ray beam axis when said bone is being drilled, said means for telescoping having a first end and a second end and a multiplicity of interconnected cylindrical tubular portions of different sizes which can be pushed together and means for coupling said first end with said coupling fitting and means for simultaneously to engaging at said second end an item selected from the group consisting of said entrance window of said image converter and said housing of said X-ray source, such that the axis of said means for telescoping is movable and is coaxial with the axis of said distal locking bore.

2. The device according to claim 1 wherein an engagement disk suitable for engagement with said housing of said X-ray source is located at said second end of said means for telescoping.

3. The device according to claim 2 and including also an inner cone provided at said second end of said means for telescoping for the receipt of an outer cone of said housing of said X-ray source.

4. The device according to claim 1 wherein said first end of said means for telescoping and said coupling fitting are coupled by means of a quick-connection coupling.

5. The device according to claim 1 and including also a drill bit and a handle attached to a sleeve-like target member having a conical portion with an opening at a smallest conical diameter of said conical portion corresponding substantially to the outer diameter of said drill bit.

6. The device according to claim 5 wherein said target member has a cylindrical portion located adjacent said conical portion and an accommodation sleeve for a guide sleeve located between said handle and said target member.

7. The device according to claim 6 and including also an auxiliary target sleeve having an outer diameter which corresponds substantially to the inner diameter of said cylindrical portion and having an inner diameter which corresponds substantially to the outer diameter of said drill bit.

8. A device according to claim 3 and including also said X-ray source.

9. A device according to claim 8 and including also said associated image converter.

10. A device for drilling holes in a cortical bone for the precise implantation of a locking nail having a longitudinal axis and at least one transverse distal bore having a bore axis transverse to said longitudinal axis of said nail, said device to be used with an X-ray source having a housing and a beam axis and with an associated image converter having an entrance window lying in a plane and a window axis perpendicular to said window and to be used such that said beam axis is simultaneously co-axially aligned with said window axis and with said distal bore when a hole is being drilled in said bone, said device comprising in combination:

a drill for drilling a hole in said bone along said axis of said distal bore, said drill having a mounting element thereon;

an extendable guide capable of extension and retraction for aligning said beam axis and said axis of said distal bore and for guiding said drill simultaneously along said beam axis and said Window axis and said axis of said distal bore, said guide having a first end having a flat engagement surface to be operatively coupled to an item selected from the group consisting of said entrance window of said image converter and said housing of said X-ray source and a second end "with means for coupling to" said mounting element on said drill when a hole is being drilled in said bone, said guide including an extendable portion that extends the length of said guide along an axis parallel to said beam axis and which has a multiplicity of interconnected cylindrical tubular portions of different sizes which can be pushed together, said mounting element on said drill located thereon in a manner for positioning said drill co-axially along both said axis of said distal bore and said beam axis during both extension and retraction of said extendable guide.

11. The device according to claim 10, wherein an engagement disk suitable for engagement with said housing of said X-ray source is located at said second end of said extendable guide.

12. The device according to claim 11 and including also an inner cone provided at said second end of said extendable guide for the receipt of an outer cone of said housing of said X-ray source.

13. The device according to claim 12 wherein said first end of said extendable guide and said coupling fitting are coupled by means of a quick-connection coupling.

14. The device according to claim 13 and including also a drill bit and a handle attached to a sleeve-like target member having a conical portion with an opening at a smallest conical diameter of said conical portion corresponding substantially to the outer diameter of said drill bit.

15. The device according to claim 14 wherein said target member has a cylindrical portion located adjacent said conical portion and an accommodation sleeve for a guide sleeve located between said handle and said target member.

16. A device according to claim 11 and including also said X-ray source.

17. A device according to claim 16 and including also said associated image converter.

18. A device for precisely making holes in a cortical bone accommodating a locking nail having at least a first distal locking bore, said device comprising in combination:

(1) an X-ray source having a housing and a beam axis, (2) an associated image converter having an entrance window which has an axis, with the axis of said entrance window co-axial with the beam axis, (3) a drilling tool having
  (a) a housing,
  (b) a chuck for accommodating a drilling bit located on the housing and
  (c) a coupling fitting located on said housing opposite to said chuck and (4) tubular guide means for guiding said drilling tool, said guide means having a longitudinal axis and including further means for freely telescopically extending said guide means along said longitudinal axis, said means for telescopically extending having a first end and a second end "with means for coupling" said first end with said coupling fitting located on said housing and "means for simultaneously engaging" said second end a part selected from the group consisting of said entrance window of said image converter and said housing of said X-ray source such that the axis of said guide means is coaxial simultaneously when said bone is being drilled with both said beam axis and said axis of said entrance window.

\* \* \* \* \*